United States Patent
Hero, III et al.

(10) Patent No.: US 7,853,432 B2
(45) Date of Patent: Dec. 14, 2010

(54) METHOD AND APPARATUS FOR CLUSTERING AND VISUALIZATION OF MULTICOLOR CYTOMETRY DATA

(75) Inventors: Alfred Hero, III, Ann Arbor, MI (US);
Kevin Carter, Ann Arbor, MI (US);
Raviv Raich, Corvallis, OR (US);
William Finn, Dexter, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 12/243,448

(22) Filed: Oct. 1, 2008

(65) Prior Publication Data
US 2009/0097733 A1   Apr. 16, 2009

Related U.S. Application Data

(60) Provisional application No. 60/997,388, filed on Oct. 2, 2007.

(51) Int. Cl.
*G01N 33/48* (2006.01)
*G06F 17/18* (2006.01)
*G06F 19/00* (2006.01)

(52) U.S. Cl. .......................... 702/181; 702/21; 702/190
(58) Field of Classification Search ................. 702/181, 702/190, 21
See application file for complete search history.

(56) References Cited

U.S. PATENT DOCUMENTS 6,134,541 A    10/2000   Castelli et al. ................. 707/2

2003/0224344 A1*   12/2003   Shamir et al. ................. 435/4
2007/0100880 A1     5/2007   Buscema ................. 707/104.1

FOREIGN PATENT DOCUMENTS

| KR | 0007306   | 1/2005  |
|----|-----------|---------|
| WO | 02/093810 | 11/2002 |

OTHER PUBLICATIONS

Shaohua Kevin Zhou et al., "From Sample Similarity to Ensemble Similarity: Probabilistic Distance Measures in Reproducing Kernel Hilbert Space", IEEE Transactions on Pattern Analysis and Machine Intelligence, vol. 28, No. 6, Jun. 2006.
Qing T. Zeng et al., "Feature-guided clustering of multi-dimensional flow cytometry datasets", ScienceDirect, Journal of Biomedical Informatics 40 (2007) 325-331, available online Jun. 27, 2006.
Sang-Mook Lee et al., "Dimensionality Reduction and Clustering on Statistical Manifolds", Computer Vision and Pattern Recognition, 2007. CVPR '07. IEEE Conference. Publicataion Date: Jun. 17-22, 2007.

* cited by examiner

*Primary Examiner*—Hal D Wachsman
*Assistant Examiner*—Janet L Suglo
(74) *Attorney, Agent, or Firm*—Harness, Dickey & Pierce, P.L.C.

(57) ABSTRACT

A computer implemented method is provided for clustering and visualization of an n-dimensional space in a Euclidean space. The method includes: collecting a plurality of multi-dimensional data sets; estimating a probability density function from each data set; approximating a dissimilarity between every pair of said probability density functions and recording every dissimilarity in a dissimilarity matrix; embedding the dissimilarity matrix into a Euclidean space having a dimensionality of three or less using a multi-dimensional scaling method; and graphically displaying relationships between data sets using data in the Euclidean space on a display of a computing device.

26 Claims, 4 Drawing Sheets

METHOD AND APPARATUS FOR CLUSTERING AND VISUALIZATION OF MULTICOLOR CYTOMETRY DATA

CROSS-REFERENCE TO RELATED APPLICATIONS

This application claims the benefit and priority of U.S. Provisional Application No. 60/997,388, filed on Oct. 2, 2007. The entire disclosures of the above applications are incorporated herein by reference.

GOVERNMENT RIGHTS

This invention was made with government support under CCR-0325571 awarded by the National Science Foundation. The U.S. Government has certain rights in the invention.

FIELD

The present disclosure relates to a method for clustering, classifying and visualization of multi-dimensional data.

BACKGROUND

The fields of statistical learning and machine learning are used to study problems of inference, which is to say gaining knowledge through the construction of models in order to make decisions or predictions based on observed data. In some problems, the observations can be represented as points in a Euclidean space with the $L_2$-norm as a natural dissimilarity metric. Solutions to problems of dimensionality reduction, clustering, classification, and other learning tasks have been formulated using the Euclidean representation. Unfortunately, when no obvious natural Euclidean representation for the data is available, such inference tasks require independent solutions.

A straightforward strategy is to express the data in terms of a low dimensional feature vector for which the curse of dimensionality is alleviated. This initial processing of data as real-valued feature vectors in Euclidean space, which is often carried out in ad hoc manner, has been called the "dirty laundry" of machine learning. This procedure is highly dependent on having a good model for the data and in the absence of such model may be highly suboptimal, resulting in much information loss. When a statistical model is available, the process of obtaining a feature vector can be done optimally by extracting the model parameters for a given data set and thus characterizing the data through its lower dimensional parameter vector.

In clinical flow cytometry, cellular suspensions are prepared from patient samples (blood, bone marrow, solid tissue), and evaluated simultaneously for the presence of several expressed surface antigens and for characteristic patterns of light scatter as the cells pass through an interrogating laser. Antibodies to each target antigen are conjugated to fluorescent markers, and each individual cell is evaluated via detection of the fluorescent signal from each marker. The result is a characteristic multi-dimensional distribution that, depending on the panel of markers selected, may be distinct for a specific disease entity.

The data from clinical flow cytometry can be considered multi-dimensional both from the standpoint of multiple characteristics measured for each cell, and from the standpoint of thousands of cells analyzed per sample. Nonetheless, clinical pathologists generally interpret clinical flow cytometry results in the form of two-dimensional scatter plots in which the axes each represent one of multiple cell characteristics analyzed (up to 8 parameters per cell in routine clinical flow cytometry, and many more parameters per cell in research applications). Additional parameters are often utilized to "gate" (i.e. select or exclude) specific cell sets based on antigen expression or light scatter characteristics; however, clinical flow cytometry analysis remains a step-by-step process of 2-dimensional histogram analysis, and the multi-dimensional nature of flow cytometry is routinely underutilized in clinical practice.

Document classification is another problem that may be better understood when a document's multi-dimensional nature is taken into account. Recent work has shown interest in using dimension reduction for the purposes of document classification and visualization.

The statements in this section merely provide background information related to the present disclosure and may not constitute prior art.

SUMMARY

A computer implemented method is provided for clustering and visualization of an n-dimensional space in a Euclidean space. The method includes: collecting a plurality of multi-dimensional data sets; estimating a probability density function from each data set; approximating a dissimilarity between every pair of said probability density functions and recording every dissimilarity in a dissimilarity matrix; embedding the dissimilarity matrix into a Euclidean space having a dimensionality of three or less using a multi-dimensional scaling method; and graphically displaying relationships between data sets using data in the Euclidean space on a display of a computing device.

Further areas of applicability will become apparent from the description provided herein. The description and specific examples in this summary are intended for purposes of illustration only and are not intended to limit the scope of the present disclosure.

DRAWINGS

Figure 1:
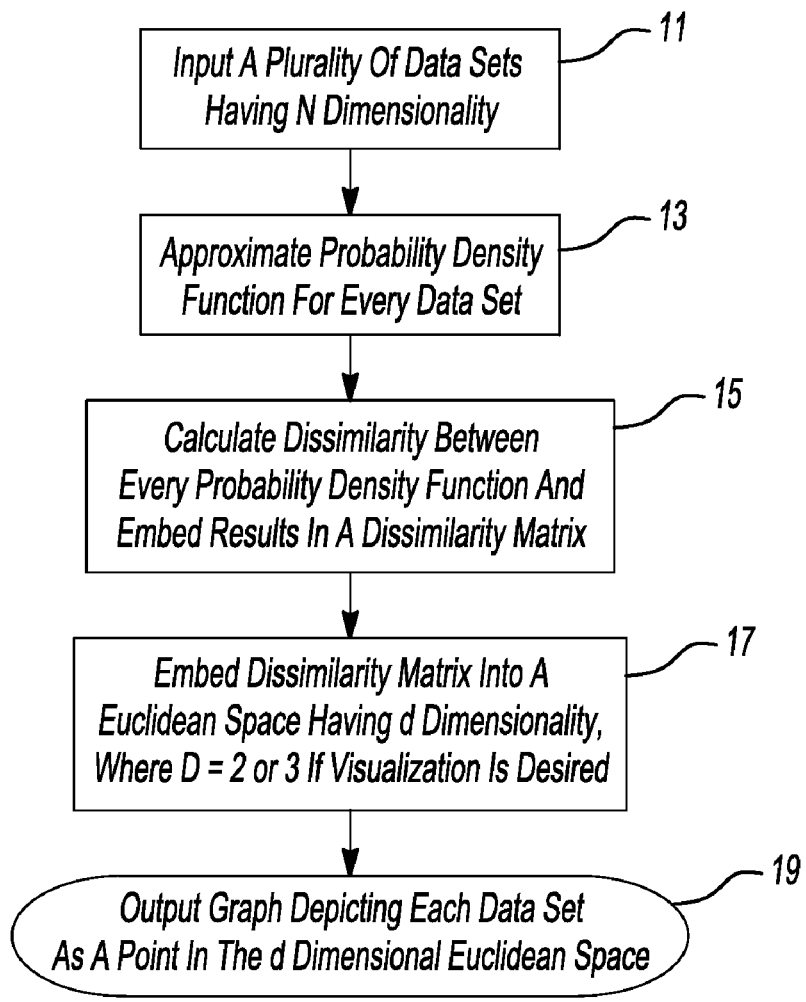
FIG. 1 illustrates a method for clustering and visualizing the relationship between multi-dimensional data sets in a low dimensional Euclidean Space.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

FIG. 1 depicts a method for clustering and visualizing a data collection consisting of sets contained in a multi-dimensional space in a two or three dimensional Euclidean Space. First, a computing device must receive a plurality of multi-dimensional data sets 11. Each data set is assumed to have been realized from some parametric model where the parameters are unknown. Using known nonparametric methods of estimating a probability density, the probability density function which defines each data set is estimated 13. Given a pair of probability density functions whose parameters are known, the Fisher information distance defines the dissimilarity or geodesic distance between the probability density functions. When the parameters of the probability density functions are unknown, however, an α-divergence can be used to approximate the dissimilarity or geodesic distance between two PDFs 13. By approximating the dissimilarity of every pair of PDFs, a dissimilarity matrix can be constructed. The dissimilarity matrix can then be embedded into a Euclidean space of predetermined dimensionality using a known multidimensional scaling method 15. The resulting embedding can be used to visualize the data in either a 2 or 3 dimensional Euclidean space 17. The computing device can output a graph depicting each data set as a point in the d-dimensional Euclidean space 19.

Information geometry has emerged from the study of geometrical structures on manifolds of probability distributions. It has been used for analysis in such fields as statistical inference, neural networks, and control systems. The following provides a brief background on the methods of information geometry that may be utilized in the provided disclosure.

It is important to understand the notion of statistical manifolds, or a set M whose elements are probability distributions. A probability density function (PDF) on a set X is defined as a function $p : \mathcal{X} \to \mathbb{R}$ in which $$p(x) \geq 0, \forall x \in \chi \quad (1)$$
$$\int p(x)dx = 1.$$

This pertains to the case for continuum on the set X. If X was discrete valued, however, equation (1) will still apply by replacing $\int p(x)dx=1$ with $\Sigma p(x)=1$. Considering M to be a family of PDFs on the set X, in which each element of M is a PDF which can be parameterized by θ, then M is known as a statistical model on X Specifically, let $$M=\{p(x|\theta)|\theta \in \Theta \subseteq \mathbb{R}^n\},$$

with p(x|θ) satisfying the equations in (1). Additionally, there exists a one-to-one mapping between θ and p(x|θ).

Given certain properties of the parameterization of M, such as differentiability and $C^\infty$ diffeomorphism (details of which are described in S. Amari and H. Nagaoka, *Methods of Information Geometry*, vol. 191, American Mathematical Society and Oxford University Press, 2000, Translations of mathematical monographs), the parameterization θ is also a coordinate system of M. In this case, M is known as a statistical manifold. The terms 'manifold' and 'statistical manifold' are used interchangeably hereinafter.

Figure 2:
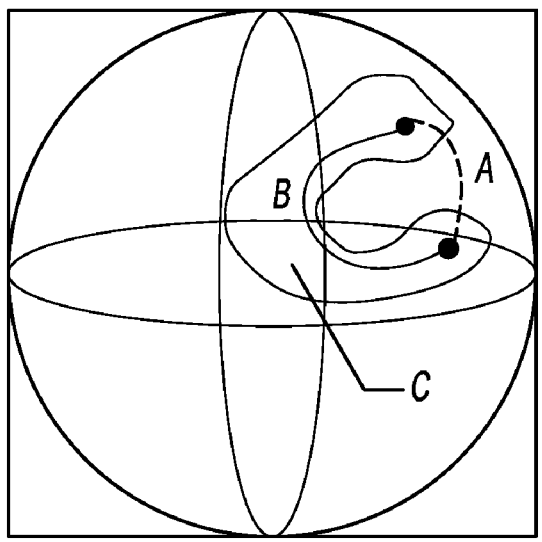
FIG. 2 is an example of a manifold which illustrates the difference between a geodesic distance and a strict probabilistic distance.

Referring to FIG. 2. In Euclidean space, the distance between two points is defined as the length of a straight line between the points. On a manifold C, however, one can measure distance by a trace of the shortest path B between the points along the manifold. This path B is called a geodesic, and the length of the path B is the geodesic distance. In information geometry, the distance between two points on a manifold C is analogous to the difference in information between them with respect to the parameterization, and is defined by the Fisher information metric. This measures the amount of information a random variable X contains in reference to an unknown parameter θ. For the single parameter case it is defined as $$I(\theta) = \left[E\left(\frac{\partial}{\partial \theta}\log f(X;\theta)\right)^2 |\theta\right].$$

If the condition $$\int \frac{\partial^2}{\partial \theta^2} f(X;\theta)dX = 0$$

is met, then the above equation can be written as $$I(\theta) = -E\left[\frac{\partial}{\partial \theta}\log f(X;\theta)\right].$$

For the case of multiple parameters $\theta=[\theta^1, \ldots, \theta^n]$, the Fisher information matrix is defined [I(θ)], whose elements consist of the Fisher information with respect to specified parameters, as $$I_{i,j} = \int f(X;\theta) \frac{\partial \log f(X;\theta)}{\partial \theta^i} \frac{\partial \log f(X;\theta)}{\partial \theta^j} dX.$$

For a parametric family of PDFs it is possible to define a Riemannian metric using the Fisher information matrix, known as the information metric. This information metric distance, or Fisher information distance, between two distributions $p(x; \theta_1)$ and $p(x; \theta_2)$ in a single parameter family is $$D_F(\theta_1, \theta_2) = \int_{\theta_1}^{\theta_2} I(\theta)^{1/2} d\theta,$$

where $\theta_1$ and $\theta_2$ are parameter values corresponding to the two PDFs and I(θ) is the Fisher information for the parameter θ. Extending to the multi-parameter case, the following is obtained:

$$D_F(\theta_1, \theta_2) = \min_{\substack{\theta(\cdot) \\ \theta(0)=\theta_1 \\ \theta(1)=\theta_2}} \int_0^1 \sqrt{\left(\frac{d\theta}{d\beta}\right)^T I(\theta)\left(\frac{d\theta}{d\beta}\right)} d\beta. \quad (3)$$

where θ(β) is the parameter path along the manifold.

The metric in (3) provides an information-based means of comparing PDFs on the appropriate statistical manifold. The shortest path θ* that minimizes (3) does so by considering only routes which lie on the manifold C, guaranteeing that each point along the path θ* is a PDF governed by M. Other distances that do not restrict measured paths to the manifold may lead to inaccurate "short cut" distances; i.e., paths that consist of PDFs not governed by M, as seen in A of FIG. 2. This is clearly the case with the $L_2$-distance, which only considers the straight-line path A between points, but is also the case for other probabilistic distances which measure the "portion of a great circle" on a hypersphere.

One property of the Fisher information metric is that it is independent of the parameterization of the manifold. Although the evaluation remains equivalent, calculating the Fisher information metric requires knowledge of the parameterization, which is generally not available in real world problems. Instead, it is assumed that the collection of density functions lies on a manifold that can be described by some natural parameterization. Specifically, one is given $p=\{p_1, \ldots, p_n\}$ where $p_i \in M$ is a PDF and M is a manifold embedded in $\mathbb{R}^d$.. In order to find an approximation for the geodesic distance between points on M using only the information available in P, one can use an approximation function G which yields:

$$\hat{D}_F(p_i, p_j) = G(p_i, p_j; P), \quad (4)$$

such that $\hat{D}_F(p_i, p_n) \to D_F(p_i, p_j)$ as $n \to \infty$.

Defining said approximation function G is similar to the setting of classical papers on manifold learning and dimensionality reduction, where only a set of points on the manifold are available. See J. B. Tenenbaum, V. de Silva, and J. C. Langford, "A global geometric framework for nonlinear dimensionality reduction," Science, vol. 290, pp. 2319-2323, 2000; and M. Belkin and P. Niyogi, "Laplacian eigenmaps and spectral techniques for embedding and clustering," in Advances in Neural Information Processing Systems, Volume 14, T. G. Diettrich, S. Becker, and Z. Ghahramani, Eds. MIT Press, 2002. As such, one can use these manifold learning techniques to construct a low-dimensional, information based embedding of that family. This not only allows for an effective visualization of the manifold (in 2 or 3 dimensions), but by embedding the family into a Euclidean space one can perform clustering of the PDFs lying on the manifold with existing Euclidean methods.

Many metrics have been defined to approximate the Fisher information distance when the specific parameterization of the manifold is unknown. An important class of such divergences is known as the $f$-divergence, in which $f(u)$ is a convex function on $u \leq 0$ and $$D_f(p\|q) = \int p(x) f\left(\frac{q(x)}{p(x)}\right).$$

A specific and important example of the $f$-divergence is the α-divergence, where $D^{(\alpha)} = D_{f^{(\alpha)}}$ for a real number α. The function $f^{(\alpha)}(u)$ is defined as $$f^{(\alpha)}(u) = \begin{cases} \frac{4}{1-\alpha^2}(1-u^{(1+\alpha)/2}) & \alpha \neq \pm 1 \\ u \log u & \alpha = 1 \\ -\log u & \alpha = -1. \end{cases}$$

As such the α-divergence can be evaluated as $$D^{(\alpha)}(p\|q) = \frac{4}{1-\alpha^2}\left(1 - \int p(x)^{\frac{1-\alpha}{2}} q(x)^{\frac{1+\alpha}{2}} dx\right) \alpha \neq 1, \text{ and}$$

$$D^{(-1)}(p\|q) = D^{(1)}(q\|p) = \int p(x) \log \frac{p(x)}{q(x)}. \quad (5)$$

The α-divergence is the basis for many important and well known divergence metrics, such as the Hellinger distance, discussed in detail below, the Kullback-Leibler divergence (5), and the Renyi-Alpha entropy (as seen in A. Renyi, "On measures of information and entropy," in *Proceedings of the 4th Berkeley Symposium on Mathematics, Statistics and Probability*, 1961, pp. 547-561). The Kullback-Leibler (KL) divergence is defined as $$KL(p\|q) = \int p(x) \log \frac{p(x)}{q(x)}, \quad (6)$$

which is equal to $D^{(-1)}$ (5). The KL-divergence is a very useful metric in information theory, and is commonly referred to as the relative entropy of a probability distribution. The following shows the relation between the Kullback-Leibler divergence and the Fisher information distance, $$\sqrt{2KL(p\|q)} \to D_F(p,q),$$

as $p \to q$.

It should be noted that the KL-divergence is not a distance metric, as it does not satisfy the symmetry, $KL(p\|q) \neq KL(p\|q)$, or triangle inequality properties of a distance metric. To obtain this symmetry, the symmetric KL divergence may be defined as:

$$D_{KL}(p,q) = KL(p\|q) + KL(q\|p), \quad (7)$$

which is still not a distance as it does not satisfy the triangle inequality. Since the Fisher information is a symmetric measure, $$\sqrt{2KL(q\|p)} \to D_F(q,p) = D_F(p,q). \quad (8)$$

Combining (7) and (8), one can approximate the Fisher information distance as:

$$\sqrt{D_{KL}(p,q)} \to D_F(p,q), \quad (9)$$

as $p \to q$. This approximation allows one to approximate the dissimilarity between to data sets, when the parameterizations of the data sets is unknown.

It is important to note that there are other methods of calculating a similarity between PDFs. The KL-divergence it is an accurate means of differentiating shapes of densities. Analysis of (6) shows that as $p(x)/q(x) \to \infty$, $KL(p\|q) \to \infty$. This property ensures that the KL-divergence will be amplified in regions where there is a significant difference in the probability distributions. As such, the difference in the tails of the distributions is a strong contributor to the KL-divergence.

As noted earlier ($\sqrt{D_{KL}(p_1,p_2)} \to D_F(p_1,p_2)$ as $p_1 \to p_2$. If $p_1$ and $p_2$ do not lie closely together on the manifold, the Kullback-Leibler divergence becomes a weak approximation of the Fisher information distance. However, a good approximation can still be had if the manifold is densely sampled between the two end points by defining the path between $p_1$ and $p_2$ as a series of connected segments, and summing the length of those segments. Specifically, given the set of n probability density functions parameterized by $P=\{\theta_1, \ldots, \theta_n\}$, the Fisher information distance between $p_1$ and $p_2$ can be approximated as $$D_F(p_1, p_2) \approx \min_{m, \{\theta_{(1)}, \ldots, \theta_{(m)}\}} \sum_{i=1}^{m} D_F(p(\theta_{(i)}), p(\theta_{(i+1)}))$$

where $p(\theta_{(1)})=p_1$, $p(\theta_{(m)})=p_2$, and $\{\theta_{(1)}, \ldots, \theta_{(m)}\} \in P$. One can then form an approximation of the Fisher information distance using the Kullback-Leibler divergence for distant points on the manifold:

$$D_F(p_1, p_2) \approx \min_{m, \{p_{(1)}, \ldots, p_{(m)}\}} \sum_{i=1}^{m} \sqrt{D_{KL}(p_{(i)}, p_{(i+1)})}$$

$$p_{(i)} \to p_{(i+1)} \forall i$$

Intuitively, this estimate calculates the length of the shortest path between points in a connected graph on the well sampled manifold.

Figure 3:
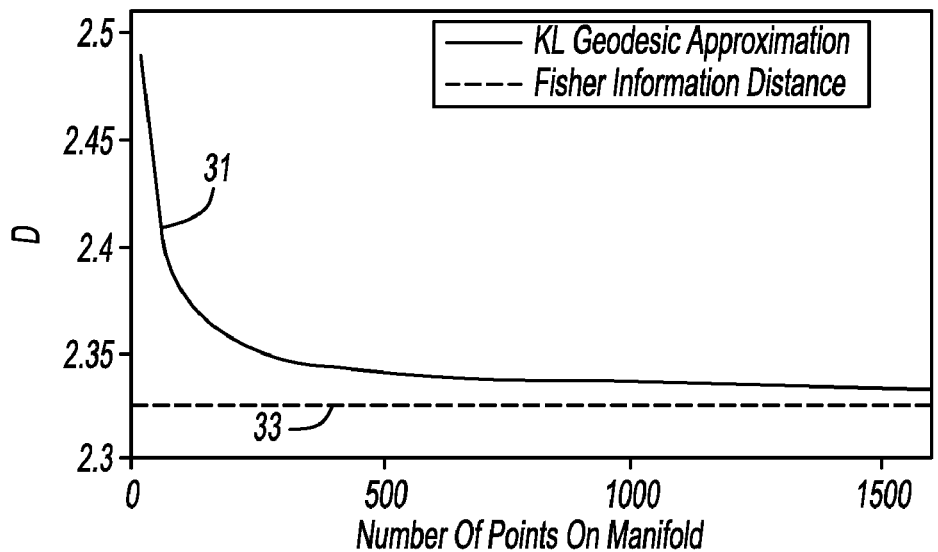
FIG. 3 is a graph demonstrating the convergence of a geodesic approximation of the Fischer information distance using the Kullback-Leibler divergence and the actual Fischer information distance as the number of sampled points increases.

Consider the 2-dimentional manifold M of univariate Gaussian PDFs parameterized by mean $\mu$ and variance $\sigma^2$. FIG. 3 illustrates this approximation by comparing the KL graph approximation 31 to the actual Fisher information distance 33. The KL-divergence between univariate normal distributions is available in a closed-form expression:

$$KL(p_1 \| p_2) = \frac{1}{2}\left(\log\left(\frac{\sigma_2^2}{\sigma_1^2}\right) + \frac{\sigma_1^2}{\sigma_2^2} + (\mu_2 - \mu_1)^2/\sigma_2^2 - 1\right),$$

while the closed-form expression for the Fisher information distance is presented in S. I. R. Costa, S. Santos, and J. Strapasson, "Fisher information matrix and hyperbolic geometry," in *Proceedings of IEEE ITSOC Information Theory Workshop on Coding and Complexity*, August 2005. As the manifold is more densely sampled (uniformly in mean and variance parameters while maintaining the same support for this simulation), the approximation converges to the true Fisher information distance 33 for the univariate normal case.

Given a matrix of dissimilarities between entities, many algorithms have been developed to find a low dimensional embedding of the original data $\psi: M \to \mathbb{R}^d$. These techniques have been classified as a group of methods referred to as multi-dimensional scaling (MDS). There are supervised methods, which are generally used for classification purposes, and unsupervised methods, which are often used for clustering and manifold learning. Using these MDS methods allows for a single low-dimensional coordinate representation of each high-dimensional, large sample data set.

Classical MDS is an unsupervised learning method that takes a matrix of dissimilarities between entities and embeds them into a Euclidean space. This is performed by first centering the dissimilarities about the origin, then calculating the singular value decomposition (SVD) of the centered matrix. This permits the calculation of the low-dimensional embedding coordinates.

Define D as a dissimilarity matrix of Euclidean distances (may also approximate Euclidean distances). Let B be the "double centered" matrix which is calculated by taking the matrix D, subtracting its row and column means, then adding back the grand mean and multiplying by $$-\frac{1}{2}.$$

As a result, B is a version of D centered about the origin. Mathematically, this process is solved by $$B = -\frac{1}{2}HD^2H,$$

where $D^2$ is the matrix of squared distances (with a slight abuse of notation), $H=I-(1/N)11^T$, I is the N-dimensional identify matrix, and 1 is an N-element vector of ones.

The embedding coordinates, $Y \in \mathbb{R}^{d \times n}$, can then be determined by the taking the eigenvalue decomposition of B, $$B = [V_1 V_2] \mathrm{diag}(\lambda_1, \ldots, \lambda_N)[V_1 V_2]^T,$$

and calculating $$Y = \mathrm{diag}(\lambda_1^{1/2}, \ldots, \lambda_d^{1/2})V_1^T.$$

The matrix $V_1$ consists of the eigenvectors corresponding to the d largest eigenvalues $\lambda_1, \ldots, \lambda_d$ while the remaining N-d eigenvectors are represented as $V_2$ refers to an diag $(\lambda_1, \ldots, \lambda_N)$ refers to N×N diagonal matrix with $\lambda_i$ as its $i^{th}$ diagonal element.

Laplacian Eigenmaps (LEM) is an unsupervised learning technique that performs non-linear dimension reduction by performing an eigenvalue decomposition on the graph Laplacian formed by the data. As such, this algorithm is able to discern low-dimensional structure in high-dimensional spaces that were previously indiscernible with methods such as principal components analysis (PCA). The algorithm contains three steps and works as follows:

1) Construct Adjacency Graph

Given dissimilarity matrix $D_x$ between data points in the set X, define the graph G over all data points by adding an edge between points i and j if $X_i$ is one of the k-nearest neighbors of $X_j$ (k is defined by the user).

2) Compute Weight Matrix W

If points i and j are connected, assign $$W_{ij} = e^{-\frac{D_x(i,j)^2}{t}}$$

otherwise $W_{ij}=0$.

3) Construct Low-Dimensional Embedding

Solve the generalized eigenvalue problem $$Lf = \lambda Df,$$

where D is the diagonal weight matrix in which $D_{ii} = \Sigma_j W_{ji}$ and L=D−W is the Laplacian matrix. If $[f_1, \ldots, f_d]$ is the collection of eigenvectors associated with d smallest generalized eigenvalues which solve the above, the d-dimensional embedding is defined by $y_i = (v_{i1}, \ldots, v_{id})^T$, $1 \leq i \leq N$.

While this disclosure only details the cMDS and LEM algorithms, there are many other methods for performing dimensionality reduction in a linear fashion (PCA) and nonlinearly (ISOMAP and Local Linear Embedding) for unsupervised learning, all of which can be applied to the disclosed method.

Thus far, a series of methods for manifold learning developed in the field of information geometry have been presented. By reducing the above described techniques into machine readable code and executing the code on a computer, dimensionality reduction on a family of data sets can be performed. This allows for better visualization and clustering of multi-dimensional data. In order to obtain a lower dimensional embedding, one can calculate a dissimilarity metric between data sets within the family by approximating the Fisher information distance between their corresponding probability densities.

In problems of practical interest, however, the parameterization of the PDFs are usually unknown. Problems of interest instead give a family of data sets $X=\{X_1, X_2, \ldots, X_N\}$. in which one may assume that each data set $X_i$ is a realization of some underlying probability distribution to which the parameters are unknown. As such, one may utilize a number of nonparametric techniques to estimate both the probability density and the approximation of the Fisher information distance. For example, one embodiment utilizes kernel density estimation (KDE) methods for deriving the probability density function estimates; although nearest neighbor methods as well as other density estimation techniques will suffice as well.

Kernel methods are non-parametric techniques used for estimating PDFs of data sets. These methods are similar to mixture-models in that they are defined by the normalized sum of multiple densities. Unlike mixture models, however, kernel methods are non-parametric and are comprised of the normalized sum of identical densities centered about each data point within the set. This yields a density estimate for the entire set in that highly probable regions will have more samples, and the sum of the kernels in those areas will be large, corresponding to a high probability in the resultant density. Given $X=[x_i, \ldots, x_n]$, where $x_{i\epsilon}\Re^d$, the kernel density estimate (KDE) of the PDF of X is defined as $$\hat{p}(x) = \frac{1}{nh}\sum_{i=1}^{n} K\left(\frac{x-x_i}{h}\right)$$

where K is some kernel satisfying the properties of a PDF and h is the bandwidth or smoothing parameter.

There are two key points to note when using kernel density estimators. First, it is necessary to determine which PDF to use as the kernel. Without a priori knowledge of the original distribution, one can use Gaussian kernels, $$K(x) = \frac{1}{2\pi^{\frac{d}{2}}|\Sigma|^{\frac{1}{2}}}\exp\left(-\frac{1}{2}x^T\Sigma^{-1}x\right),$$

where $\Sigma$ is the covariance matrix, as they have the quadratic properties that will be useful in implementation. Secondly, the bandwidth parameter is very important to the overall density estimate. Choosing a bandwidth parameter too small will yield a peak filled density, while a bandwidth that is too large will generate a density estimate that is too smooth and loses most of the features of the distribution. There has been much research done in calculating optimal bandwidth parameters, resulting in many different methods which can be used in this framework. See Bernard Silverman, *Density Estimation for Statistics and Data Analysis* (*Monographs on Statistics and Applied Probability*); and John Wiley and Sons, 1986 and George Terrell, "The maximal smoothing principle in density estimation," *Journal of the American Statistical Association*, vol. 85, no. 410, pp. 470-477, June 1990, Note that the mean squared error of a KDE decreases only as $n^{-O(1/d)}$, which becomes extremely slow for a large d. As such it may be difficult to calculate good kernel density estimates as d increases. Within this framework, however, the estimation of densities is secondary to the estimation of the divergence between them. As such, the issues with mean square error of density estimates in large dimensions are not of concern.

Using the above mentioned approximations, a computer can perform the same multi-dimensional scaling operations as previously described when dealing with families of PDFs with unknown parameterizations.

Figure 4:
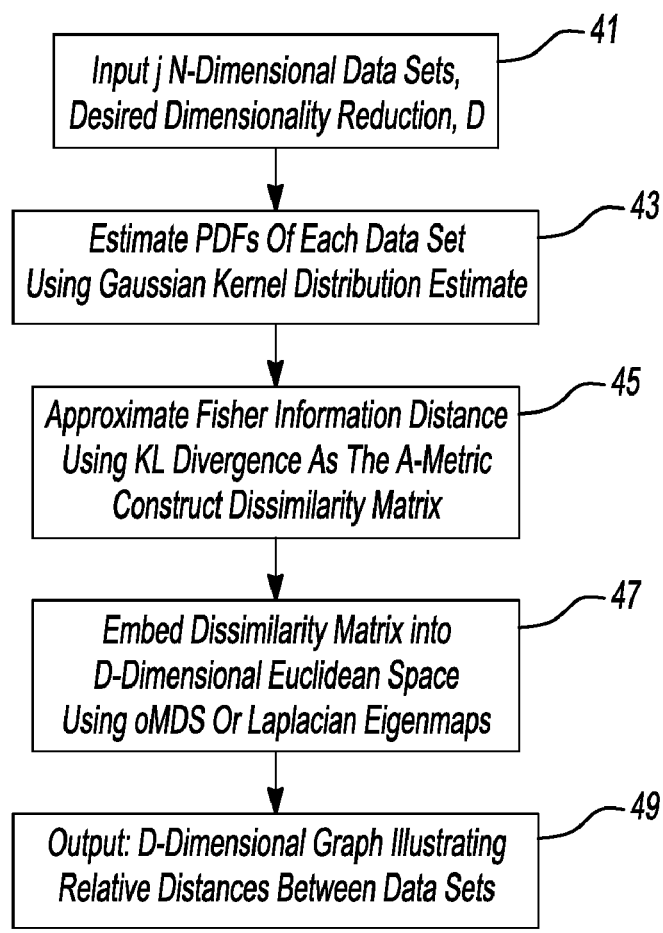
FIG. 4 illustrates an embodiment of the claimed methods.

Referring now to FIG. 4. a method is presented that combines all of the methods that have been presented in order to find a low-dimensional embedding of a collection of data sets. This method is referred hereinafter as Fisher Information Nonparametric Embedding (FINE). This method includes a characterization of high-dimensional data sets 41 in terms of a nonparametric statistical model 43, a geodesic approximation of the Fisher information distance as a metric for evaluating similarities between data sets 45, and a dimensionality reduction procedure to obtain a low-dimensional Euclidean embedding 45 of the original high-dimensional data set for the purposes of both classification and visualization 47. Presuming that each data set is a realization of an underlying probability density, and each of those densities lies on a manifold with some natural parameterization, then this embedding can be viewed as an embedding of the actual manifold into Euclidean space. Note that in line 5 below, embed(G; d) 47 refers to using any multi-dimensional scaling method (such as Isomap, cMDS, Laplacian Eigenmaps, etc) to embed the dissimilarity matrix into a Euclidean space with dimension d. The method may output a d-dimensional graph illustrating relative distances between data sets 49. It is important to stress that the FINE method does not require any a priori knowledge of a data set.

---

Fisher Information Nonparametric Embedding (FINE)

---

Input: Collection of data sets X = $\{X_1, X_2, \ldots, X_n\}$; the desired embedding dimension d
1:    for i = 1 to N do
2:        Calculate $\hat{p}(x)$, the density estimate of Xi
3:    end for
4:    Calculate dissimilarity matrix G, where G(i; j) is the geodesic approximation of the Fisher information distance between pi and pj
5:    Y = mds(G; d)
Output: d-dimensional embedding of X, into Euclidean space $Y \in \mathbb{R}^{d \times n}$

---

Many problems of practical interest involve data sets which are not naturally represented in Euclidean space. Due to the curse of dimensionality it is difficult to both visualize and find a natural separation within the data for clustering purposes. This disclosure presents the FINE framework, which may be used to solve both of these problems. By using methods from information geometry, a computer can learn the manifold from which the probability distributions governing the data lie. Moreover the FINE framework allows a computer to find a low-dimensional embedding of the manifold, which allows it to not only find the natural separation and clustering of the data, but to also reconstruct the original manifold and display it in a low-dimensional space.

While the embodiments presented express the use of the Kullback-Leibler divergence as our dissimilarity measure, it is important to stress the FINE method is not tied to it. Many other methods of determining a 'distance' between probability distributions fit within this framework. For example, when dealing with high-dimensional, sparse data sets (such as term-frequencies in document classification), the KL-divergence is not an appropriate measure, due to divide-by-zero issues. In this case, the Hellinger distance may be more representative.

The Hellinger distance is another important result of the α-divergence is the evaluation with α=0:

$$D^{(0)}(p\|q) = 2\int (\sqrt{p(x)} - \sqrt{q(x)})^2 dx,$$

which is called the closely related to the Hellinger distance, $$D_H = \sqrt{\frac{1}{2}D(0)},$$

which satisfies the axioms of distance–symmetry and the triangle inequality. The Hellinger distance is related to the information distance in the limit by $$2D_H(p,q) \to D_F(p,q)$$

as p→q [21]. We note that the Hellinger distance is related to the Kullback-Leibler divergence as in the limit $\sqrt{KL(p\|q)} \to D_H(p,q)$.

The FINE framework may be applied to any real data sets coming from unknown underlying probability distributions. This will include document classification, internet anomaly detection, as well as biological problems. The FINE method can be used for a variety of different learning problems as long as the problem can be formatted into the following setting: large sample size data sets derived from an underlying probability distribution in which the parameterization is unknown.

Figure 5:
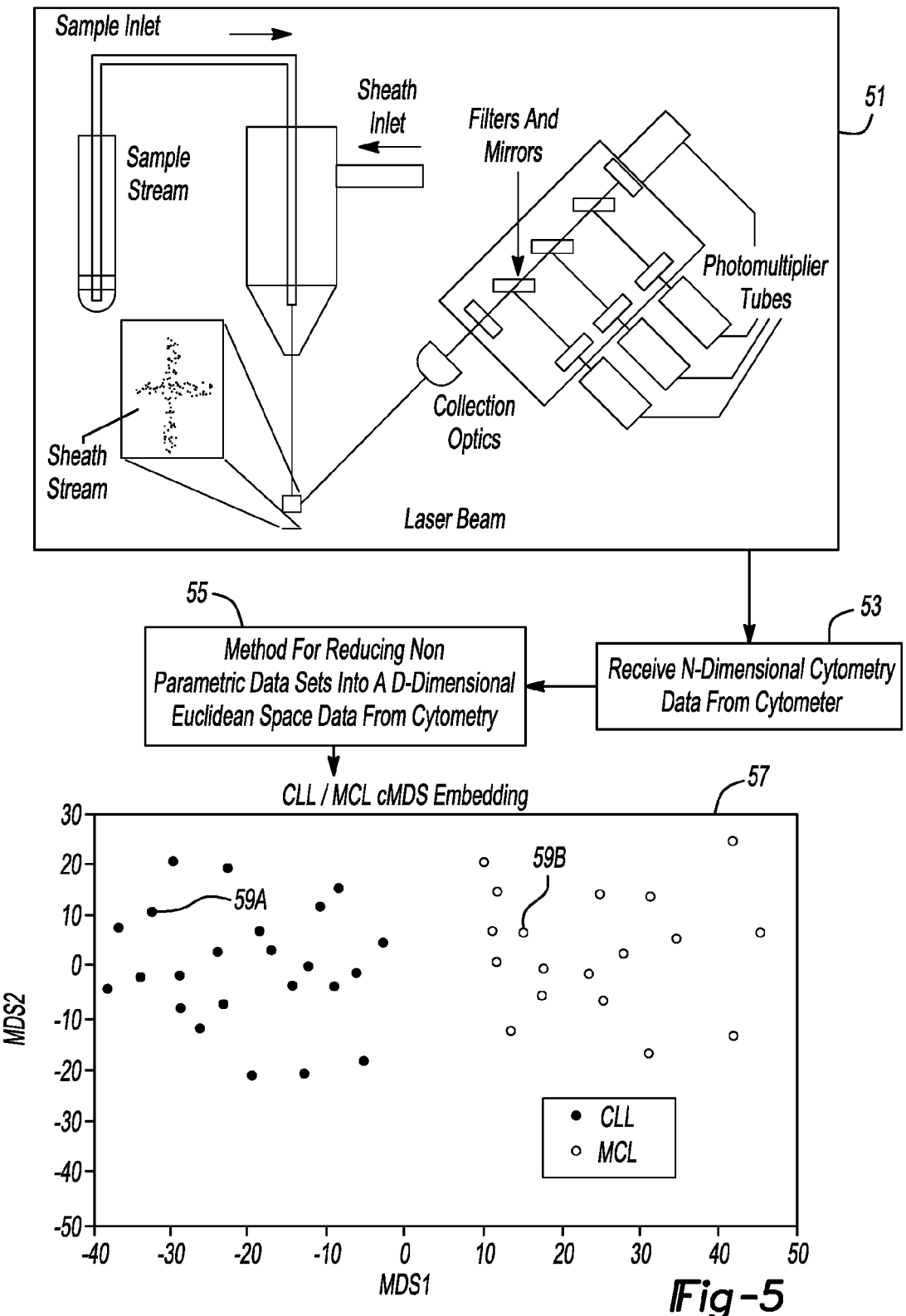
FIG. 5 is a diagram demonstrating the use of Fisher information non parametric embedding to analyze cytometry data.

Referring now to FIG. 5. Applying this framework to the practice of cytometry, it is potentially beneficial, therefore, to develop systems of clustering and classification of clinical flow cytometry data 53 that utilize all dimensions of data derived for each cell during routine clinical analysis. Applying the disclosed method 55 to clinical flow cytometry 51, the FINE method allows observers to differentiate between two different samples that display similar characteristics 57 when analyzed using traditional comparison techniques. For example, compare patients with two distinct, but immunophenotypically similar forms of lymphoid leukemia, mantle cell lymphoma (MCL) and chronic lymphocytic leukemia (CLL). These diseases display similar characteristics with respect to many expressed surface antigens, but are distinct in their patterns of expression of two common B lymphocyte antigens CD23 and FMC7 (a distinct conformational epitope of the CD20 antigen). Typically, CLL is positive for expression of CD23 and negative for expression of FMC7, while MCL is positive for expression of FMC7 and negative for expression of CD23. These distinctions lead to a difference in densities between patients in each disease class, and should show a natural clustering 59A and B.

Defining $X=\{X_1, X_2, \ldots, X_n\}$ where $X_i$ is the data set corresponding to the flow cytometer output of the $i^{th}$ patient. Each patient's blood is analyzed for 5 parameters: forward and side light scatter, and 3 fluorescent markers (CD45, CD23, FMC7). Hence, each data set X is 5-dimensional with $n_i$, elements corresponding to individual blood cells (each $n_i$ may be different). Given that X is comprised of both patients with CLL and patients with MCL, this example demonstrates the performance of an embodiment of this disclosure, where the MDS is an unsupervised classification algorithm.

In this example, the data set consists of 23 patients with CCL and 20 patients with MCL. The set $X_i$ for each patient is on the order of $N_i \approx 5000$ cells. FIG. 5 shows a 2-dimensional embedding of 5-dimensional cytometry data sets, using cMDS, with the Kullback-Leibler divergence set as the dissimilarity metric. Each point in the plot 57 represents an individual patient. Although the discussed methods perform the dimensionality reduction and embedding in unsupervised methods, the class labels have been provided as means of demonstration. It should be noted that there exists a natural separation between the different classes. As such, one can conclude that there is a natural difference in probability distribution between the disease classes as well. Although this specific classification has been observed through years of clinical experience, one can quickly determine this without any a priori knowledge, simply by utilizing Fisher-information Non-Parametric Embedding methods.

Raw flow cytometry data for this example was generated by analysis on a Beckman-Coulter FC-500 flow cytometer using Beckman-Coulter CXP acquisition software (Beckman-Coulter, Hialeah, Fla.) and stored as list mode data in standard fcs format. However, other flow cytometers can be used to obtain similar results.

Figure 6:
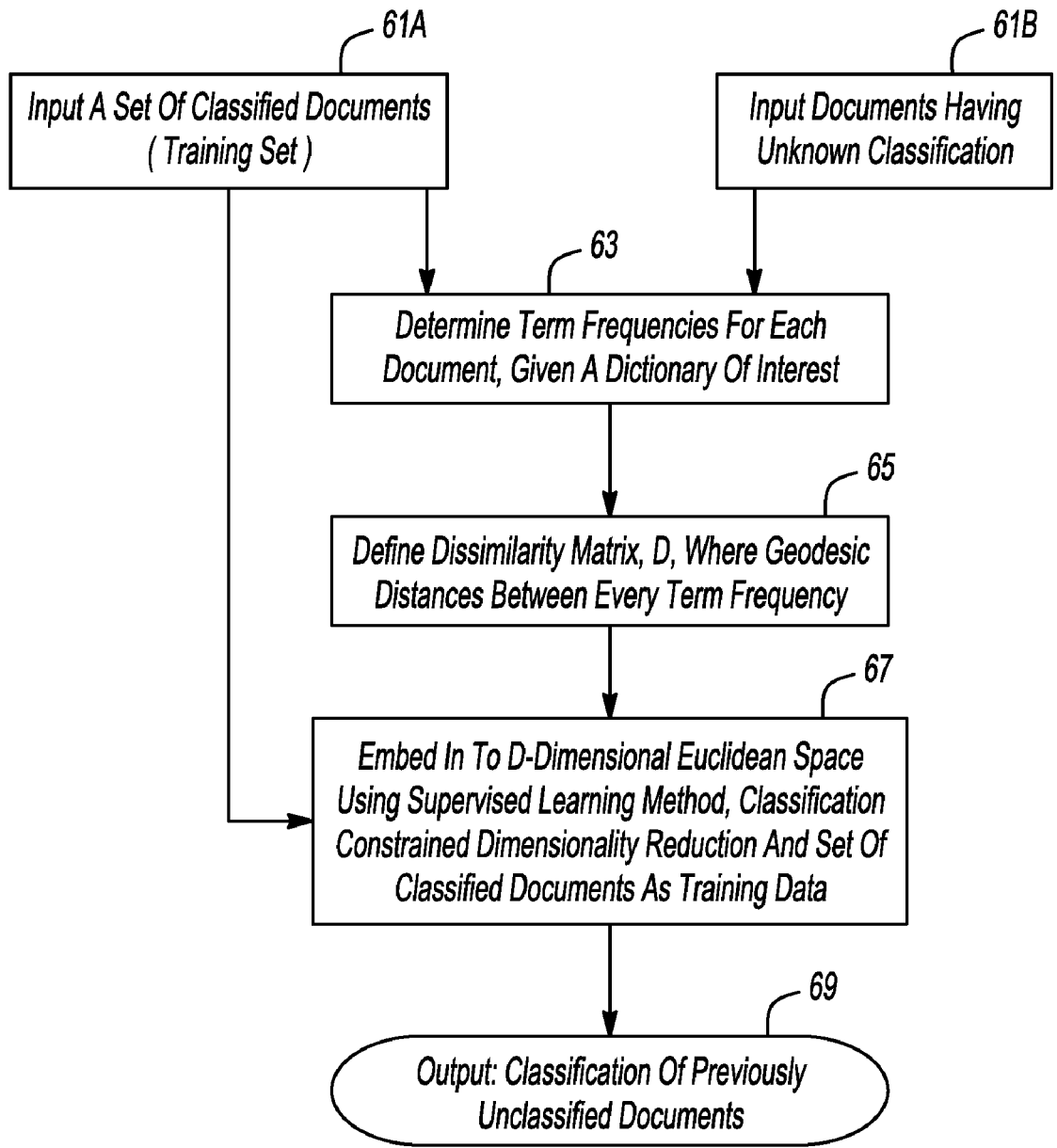
FIG. 6 is a diagram demonstrating the use of Fisher information non parametric embedding to classify unknown documents.

Referring to FIG. 6. Similarly, document classification presents a problem of high-dimensionality without an efficient means of classification. Typically documents 61A and B are represented as very high dimensional PDFs, and learning algorithms suffer from the curse of dimensionality. Dimension reduction not only alleviates these concerns, but it also reduces the computational complexity of learning algorithms due to the resultant low-dimensional space. As such, the problem of document classification is an interesting application for FINE.

Given a collection of documents of known class 61A, one may wish to best classify documents of unknown class 61B. A document can be viewed as a realization of some overriding probability distribution 63, in which different distributions will create different documents. For example, in a newsgroup about computers one could expect to see multiple instances of the term "laptop", while a group discussing recreation may see many occurrences of "sports". The counts of "laptop" in the recreation group, or "sports" in the computer group would predictably be low. As such, the distributions between articles in computers and recreation should be distinct. In this setting, one may define the PDFs as the term frequency representation of each document. Specifically, let $x_i$ be the number of times term i appears in a specific document. The PDF of that document can then be characterized as the multinomial distribution of normalized word counts, with the maximum likelihood estimate provided as $$\hat{p}(x) = \left( \frac{x_1}{\sum_i x_i}, \ldots, \frac{x_n}{\sum_i x_i} \right) \tag{10}$$

where n is the number of words in the dictionary of interest.

By utilizing the term frequencies as multinomial distributions, and not implementing a kernel density estimator, it will be apparent that the FINE methods are not tied to the KDE, but in the case of continuous densities it can be used as a means of estimation. Additionally, the Hellinger distance may be used to approximate the geodesic distances due to the multinomial nature of the distribution. A dissimilarly matrix, D, can be defined whose elements may include the geodesic distances between each term frequency 65. The dissimilarity matrix can then be embedded into ad-dimensional Euclidean space 67.

The following example utilizes the well known 20 Newsgroups data set, which is commonly used for testing document classification methods. This set contains word counts for postings on 20 separate newsgroups. This example restricts the simulation to the 4 domains with the largest number of sub-domains (comp.*, rec.*, sci.*, and talk.*), and will classify each posting by its highest level domain. Specifically we are given P={$p_i \ldots p_N$} where each $p_i$ corresponds to a single newsgroup posting and is estimated with (10). It is noted that the data can be preprocessed to remove all words that occur in 5 or less documents for the purpose of optimization Within the classification framework in general, one can utilize either supervised or unsupervised learning methods to reduce dimensionality. Unsupervised methods may be used to determine if a natural separating geometry exists between domains. The unsupervised methods disclosed above may be applied to the task of document classification.

By configuring FINE to use supervised methods for embedding, one can dramatically improve classification performance. By embedding with Classification Constrained Dimensionality Reduction (CCDR), see Raich, J. A. Costa, and A. O. Hero, "On dimensionality reduction for classification and its applications," in *Proc. IEEE Intl. Conference on Acoustic Speech and Signal Processing*, May 2006, which is essentially LEM with an additional tuning parameter defining the emphasis on class labels in the embedding.

Once dimensionality has been reduced, the unknown documents can be classified based on their proximity to the clusters of known documents 69. Algorithms such as linear kernel support vector machines, and support vector machines in general, may be implemented to choose a classification for the unknown document once the data sets have been embedded into a Euclidean space. See Hyunsoo Kim, Peg Howland, and Haesun Park, "Dimension reduction in text classification with support vector machines," in *Journal of Machine Learning Research* 6, January 2005, pp. 37-53; and C.-C. Chang and C.-J. Lin, LIBSVM: A library for support vector machines, 2001.

While our focus when using a supervised FINE implementation has been on jointly embedding both the training and test samples (while keeping the test samples unlabeled), an alternative embodiment implements out of sample extension (OOS) with FINE. In this scenario, the training samples are embedded as normal with CCDR, while the test samples are embedded into the low-dimensional space using interpolation. This setting allows for a significant decrease in computational complexity given the fact that the FINE embedding has already been determined for the training samples (i.e. new test samples are received). A decrease in performance exists when compared to the jointly embedded FINE, which is reduced as the number of training samples increases.

In conclusion, the assumption that high-dimensional data lies on a Euclidean manifold is based on the ease of implementation due to the wealth of knowledge and methods based on Euclidean space. This assumption is not viable in many problems of practical interest, as there is often no straightforward and meaningful Euclidean representation of the data. In these situations it is more appropriate to assume the data is a realization of some PDF which lies on a statistical manifold. Using information geometry, one now has the ability to find a low-dimensional embedding of the manifold, which allows a user to not only find the natural separation of the data, but to also reconstruct the original manifold and visualize it in a low-dimensional Euclidean space. This allows the use of many well known learning techniques which work based on the assumption of Euclidean data.

By approximating the Fisher information distance, FINE is able to construct the Euclidean embedding with an information based metric, which is more appropriate for non-Euclidean data. This disclosure has illustrated this approximation by finding the length of the geodesic along the manifold, using approximations such as the Kullback-Leibler divergence and the Hellinger distance. The specific metric used to approximate the Fisher information distance is determined by the problem, and FINE is not tied to any specific choice of metric. Additionally, it is noted that that although we utilize kernel methods to obtain PDFs, the method used for density estimation is only of secondary concern. The primary focus is the measure of dissimilarity between densities, and the method used to calculate those PDFs is similarly determined by the problem.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A computer implemented method for clustering and visualization of an n-dimensional space in a Euclidean space, comprising:

collecting a plurality of multi-dimensional data sets;

estimating a probability density function from each data set;

approximating a dissimilarity between every pair of said probability density functions and recording every dissimilarity in a dissimilarity matrix;

embedding the dissimilarity matrix into a Euclidean space having a dimensionality of three or less using a multi-dimensional scaling method, where the steps of estimating, approximating and embedding are executed by a processor of a computing device; and graphically displaying relationships between data sets using data in the Euclidean space on a display of the computing device.

2. The method of claim 1 further comprising estimating the probability density function using a nonparametric method.

3. The method of claim 2 wherein the nonparametric method is a kernel density estimation method.

4. The method of claim 1 further comprising approximating the dissimilarity between every pair of probability density functions using a divergence metric.

5. The method of claim 4 wherein the divergence metric estimates of a Fisher information distance.

6. The method of claim 5 further comprising approximating the Fisher Information Distance using a Kullback-Leibler divergence.

7. The method of claim 5 further comprising approximating the Fisher Information Distance using a Hellinger distance.

8. The method of claim 1 wherein the multi-dimensional scaling method is an unsupervised multi-dimensional scaling method.

9. The method of claim 8 wherein the multi-dimensional scaling method is Laplacian Eigenmaps.

10. The method of claim 8 wherein the multi-dimensional scaling method is Classical Multi Dimensional Scaling.

11. The method of claim 1 wherein a parametric method is used to estimate the probability density functions.

12. The method of claim 11 further comprising approximating the dissimilarities between probability density functions using the Fisher information distance.

13. A computer implemented method for clustering and visualization of multicolor flow cytometry data comprising:
receiving blood samples from a plurality of patients;
analyzing the blood samples using a flow cytometer, thereby yielding a multi-dimensional data set for each blood sample;
estimating a probability density function for each data set using a non parametric method;
determining a geodesic distance between each pair of probability density functions using a divergence metric to estimate the distance;
organizing said geodesic distances in a dissimilarity matrix;
embedding said dissimilarity matrix in a Euclidean space using a multi-dimensional scaling method, where the steps of estimating, determining, organizing, and embedding are executed by a processor of a computing device; and
graphically displaying relationships between data sets in the Euclidean space.

14. The method of claim 13 further comprising estimating the probability density function using a kernel density estimation method.

15. The method of claim 13 further comprising determining the geodesic distance using a Kullback-Leibler divergence.

16. A computer implemented method for classifying an unknown multi-dimensional data set into a predetermined classification based on the proximity of the unknown data set to the clusterings of the predetermined classifications in a reduced space, comprising:
collecting a plurality of multi-dimensional data sets of predetermined classifications;
collecting a data set of unknown classification;
estimating a probability density function from each data set, wherein said probability density function estimates a model for producing the corresponding data set;
approximating a dissimilarity between every pair of said probability density functions and recording every dissimilarity in a dissimilarity matrix;
embedding the dissimilarity matrix into a Euclidean space of predetermined dimensionality using a multi-dimensional scaling method, wherein a cluster of data sets may be realized for each predetermined classification, where the steps of estimating, approximating and embedding are executed by a processor of a computing device; and
classifying said data set of unknown classification into one of the predetermined classifications based on the proximity of the data set of unknown classification to the clusters of classified data sets, wherein the data set of unknown classification is classified with the cluster of data sets which it is in closest proximity to in the reduced space.

17. The method of claim 16 wherein the multi-dimensional scaling method includes a supervised learning method, wherein a training set is used by the supervised learning method to define an output for unknown data sets.

18. The method claim of 17 wherein the training set comprises at least a portion of the data sets of predetermined classifications.

19. The method of claim 18 wherein the data set of unknown classification is used as training data after it has been classified.

20. The method claim of 17 wherein the supervised method for learning is Classification Constrained Dimensionality Reduction.

21. A computer implemented method for classifying documents of unknown classification into one of a plurality of predetermined classifications comprising:
collecting a plurality of documents, wherein each document is stored in an electronic format and has a predetermined classification;
collecting at least one document of unknown classification and storing the document of unknown classification in an electronic format;
defining a dictionary of interest having n entries, wherein n is the number of words in the dictionary of interest;
determining a term frequency of each document;
approximating the geodesic distance between every pair of term frequencies and storing said geodesic distances in a dissimilarity matrix;
embedding said dissimilarity matrix in a d dimensional Euclidean space, wherein d is the desired dimension;
determining a cluster in the d dimensional Euclidean space for each predetermined classification;
comparing proximities of the document of unknown classification to the clusters of documents having predetermined classifications in the d dimensional space;
determining which cluster is in the greatest proximity to the document of unknown classification; and
classifying the document of unknown classification as the predetermined classification of the cluster which has the greatest proximity to the document of greatest proximity.

22. The method of claim 21 wherein the dissimilarity matrix is embedded in a d dimensional Euclidean space using a supervised learning technique.

23. The method of claim 22 wherein the supervised learning technique is Classification Constrained Dimensionality Reduction.

24. The method of claim 22 wherein the documents of known classification are used as a training set.

25. The method of claim 24 wherein the document of unknown classification is a member of the training set once said document has been correctly classified.

26. The method of claim 21 further comprising determining which cluster is in the greatest proximity to the document of unknown classification using linear kernel support vector machines.

* * * * *

UNITED STATES PATENT AND TRADEMARK OFFICE
CERTIFICATE OF CORRECTION

PATENT NO. : 7,853,432 B2
APPLICATION NO. : 12/243448
DATED : December 14, 2010
INVENTOR(S) : Alfred Hero, III et al.

It is certified that error appears in the above-identified patent and that said Letters Patent is hereby corrected as shown below:

Column 2, line 45 "Space" should be --space--.

Column 2, line 57 "non parametric" should be --nonparametric--.

Column 2, line 60 "non parametric" should be --nonparametric--.

Column 3, line 5 "Space" should be --space--.

Column 3, line 50 after "X", insert --.--.

Column 4, line 27 "$\partial$" should be --$\partial^2$--.

Column 4, line 27 "$\partial\theta$" should be --$\partial\theta^2$--.

Column 5, line 19 "p=" should be --P=--.

Column 5, line 60 "$\mu$" should be --u--.

Column 6, line 51 "to data sets" should be --two data sets--.

Column 6, line 54 after "KL-divergence", delete "it".

Column 10, line 7 "June 1990," should be --June 1990.--.

Column 10, line 20 "FIG. 4. a" should be --FIG. 4. A--.

Column 10, line 37 "embed(G; d)" should be --'embed(G; d)--.

Column 12, line 3 "X" should be --$X_i$--.

Column 12, line 11 "$N_i$" should be --$n_i$--.

Column 13, line 10 "ad-dimensional" should be --a d-dimensional--.

Signed and Sealed this
Thirtieth Day of August, 2011

David J. Kappos
*Director of the United States Patent and Trademark Office*

CERTIFICATE OF CORRECTION (continued)
U.S. Pat. No. 7,853,432 B2

Column 13, lines 12-13 "Newsgroups" should be --newsgroups--.

Column 13, lines 22-23 After "optimization", insert --.--.

Column 14, line 21 delete second occurrence of "that".

Column 14, line 64, Claim 5, after "estimates", delete "of".

Column 15, line 23, Claim 13, "non parametric" should be --nonparametric--.

Column 16, line 10, Claim 18, "claim of" should be --of claim--.

Column 16, line 16, Claim 20, "claim of" should be --of claim--.

Column 16, line 48, Claim 22, "d dimensional" should be --d-dimensional--.